United States Patent [19]

Bolliger et al.

[11] Patent Number: 4,979,611
[45] Date of Patent: Dec. 25, 1990

[54] INDIVIDUAL PACKAGE FOR ORTHODONTIC BRACKET

[75] Inventors: Diane K. Bolliger, San Diego; Ralph Strahan, Ramona, both of Calif.

[73] Assignee: Johnson & Johnson Consumer Products, Inc., New Brunswick, N.J.

[21] Appl. No.: 437,956

[22] Filed: Nov. 16, 1989

Related U.S. Application Data

[63] Continuation-in-part of Ser. No. 325,712, Mar. 20, 1989, abandoned.

[51] Int. Cl.⁵ ............................................. A61C 19/10
[52] U.S. Cl. .................................. 206/83; 206/0.84; 206/461; 206/460
[58] Field of Search .................... 206/0.83, 0.84, 461, 206/471, 438, 460, 83

[56] References Cited

U.S. PATENT DOCUMENTS

| | | | |
|---|---|---|---|
| 2,571,073 | 10/1951 | Stroop | 206/449 |
| 3,407,928 | 10/1968 | Watts, Jr. | 206/78 |
| 3,424,380 | 1/1969 | Curran | 239/60 |
| 4,083,451 | 4/1978 | Hair | 206/461 |
| 4,380,291 | 4/1983 | Shannon | 206/343 |
| 4,385,688 | 5/1983 | Grant | 206/0.84 |
| 4,466,534 | 8/1984 | Dunn | 206/45.34 |
| 4,632,247 | 12/1986 | Moodey et al. | 206/343 |

Primary Examiner—Joseph Man-Fu Moy
Attorney, Agent, or Firm—Paul A. Coletti

[57] ABSTRACT

A holder for dental brackets having a frame which has an adhesive face on one side. The frame is foldable around a central line. Within each part of the frame is a transparent plastic. Thus, the dental brackets fit within the transparent plastic pouch formed by the frame and are manageable, identifiable, and remain sanitarily safe during transport. In addition, the stackable nature of the frame makes them easier to store.

8 Claims, 3 Drawing Sheets 4,979,611

INDIVIDUAL PACKAGE FOR ORTHODONTIC BRACKET

The current invention is a continuation-in-part of Ser. No. 325,712, filed Mar. 20, 1989, now abandoned.

FIELD OF THE INVENTION

The present invention relates to holders for dental brackets. More specifically, the present invention relates to individual packets for dental brackets. Most specifically, the present invention relates to individual holders for dental brackets for identification and sanitary purposes.

BACKGROUND OF THE INVENTION

Clear dental brackets are extremely small objects. They measure no more than 3 centimeters across, and 3 centimeters in height. Because they are generally clear, it is difficult to see and handle them. In addition, all dental brackets commonly in use are generally of the same size and shape. Thus, it is very difficult to determine the appropriate dental bracket for the teeth on which the brackets are to be placed.

This handling and identification problem can cause delays in both time and cost. It is therefore desirable to have a dental bracket holder which also eases the handling and identification of the bracket.

In addition, it is also difficult to keep dental brackets hygienically clean before emplacement on the teeth. This is important due to their small size and the tendency to keep all the brackets in one place. Therefore, it is also desirable to incorporate this sanitary feature into a dental bracket holder.

Finally, dental brackets are almost always placed on the teeth in sets. That is, when one dental bracket is put in the oral cavity, an entire group of dental brackets are placed in the mouth during the same procedure. Thus, it is desirable to not only keep dental brackets properly identified and sanitary in a holder, but also to be able to identify all the dental brackets to be used as a group.

SUMMARY OF THE INVENTION

Accordingly, these and other objects of the present invention are accomplished in a holder for dental brackets which comprises a continuous tear proof frame having adhesive coated to one side. This frame is symmetrically configured about a central line. Inside the frame there is a puncture-proof, tear-resistant, transparent sealant attached to the frame, within the boundaries formed by the frame. Thus, when a sanitary dental bracket is placed within the puncture-proof frame and the frame is folded about the central line, the sealant forms a pouch surrounding the dental bracket and the symmetrical frame parts adhere to themselves, sealing the dental bracket within the pouch. Thus, the dental bracket remains sanitary, and is easily identified on the frame, and not on the bracket itself.

A group of dental brackets may also be emplaced on a strip, which will adhesively maintain a complete set of dental brackets. Thus, the user is able to have the appropriate dental brackets adequately identified, sanitary, and packaged in an entire set, with the entire package all more readily available for use.

The objects of the present invention are readily seen in the accompanying detailed description of the drawings, and the attached detailed description of the present invention in which:

DETAILED DESCRIPTION OF THE DRAWINGS

DETAILED DESCRIPTION OF THE INVENTION

Figure 1:
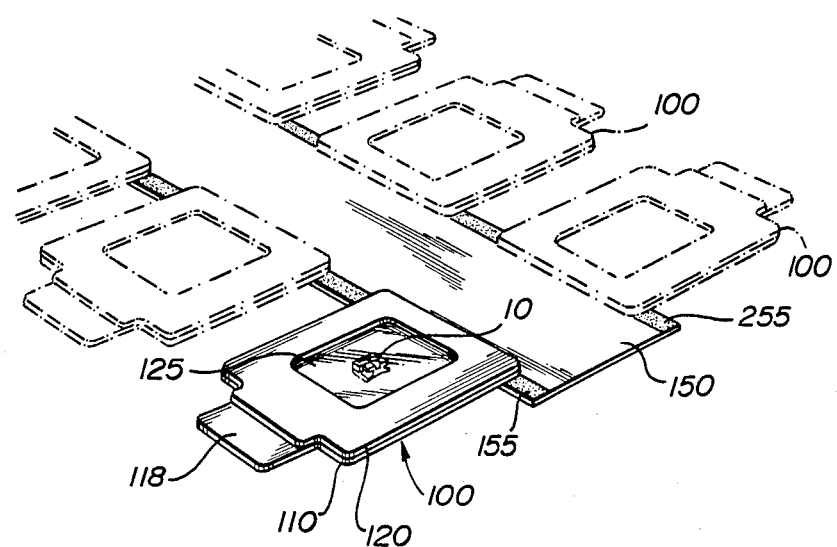
FIG. 1 is a perspective view of a closed dental bracket holder of the present invention as placed on a retaining strip in the form of a card.
Figure 2:
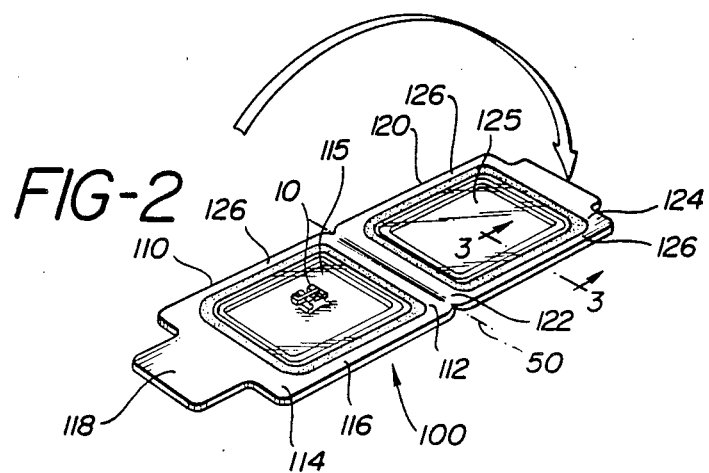
FIG. 2 is a perspective view of an opened dental bracket holder of the present invention.

As seen from the FIGS. 1-6, dental brackets 10 are extremely small. These dental brackets 10 are difficult to identify, both for their transparent nature and for their generally identical sizes, which will not vary substantially from tooth to tooth. What is needed therefore, is an identifier which will hold the dental brackets 10 and keep them hygienically and sanitarily sealed, and at the same time adequately identify the brackets. This is accomplished by the holder 100 of the present invention.

The holder 100 generally contains frames 110, 120, which are foldable about a central line 50. These frames are generally formed from a tear-proof, plastic-coated cardboard. Each of the frames 110, 120 contains bottom edges 112, 122 and tops 114, 124. These top and bottom edges are attached by a pair of sides 116, 126. The face of these frames 110, 120 which will be folded on one another is backed with an adhesive coating.

Each of these frames 110, 120 encloses a film represented as films 115, 125. This film is generally formed from a transparent tear-proof puncture-proof plastic. On one of the frames 110, there will also be a handle or tab 118.

In accordance with principles of the present invention, the dental brackets 10 are emplaced within the frame 110 upon film 115. Thereafter, the frames 110, 120 are folded about central line 50 so that they adhere to one another. When this is accomplished, the frames 110, 120 form a pouch within the film. The dental bracket 10 is adequately sealed and maintained within that pouch.

Of course, it will be appreciated that the film 115, 125 can be one continuous strip of plastic, and the bottom edges 112, 122 are entirely optional. What is necessary is at least a three-sided rectangular-shaped frame within which a pouch formed from the plastic film will adequately seal the dental bracket 10.

The dental bracket is now adequately sealed within the pouch and is easily manageable. Thus, even with hard to identify brackets, they can be pre-placed within the pouches after manufacture, and remain in the pouches until their use by the orthodontist. This prevents any confusion caused by jostling or handling of the brackets within a separate container or the like. In addition, it is also realized that because the dental brackets 10 are within the pouch formed by the film 115, 125, they also will be sanitarily sealed from the environment. Thus, any handling of the dental bracket 10 will be accomplished only by handling of the holder 100 of the present invention. This prevents unnecessary handling in the course of the use of these brackets 10.

Because the closed holders 100 of the present invention are generally thin, as seen from FIG. 1, the brackets may be emplaced within a closed box much like photographic slides. Thus, the dental brackets will be easily identifiable by the markings on the holders 100, and an entire set can be stored in one separate box within the slides.

Figure 7:
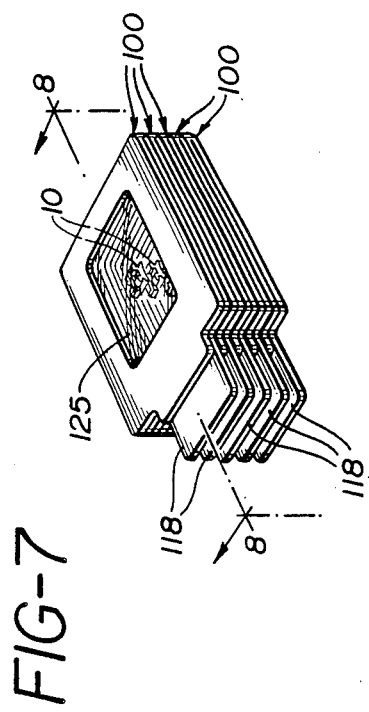
FIG. 7 is a perspective view of stacked protective devices of the invention.
Figure 8:
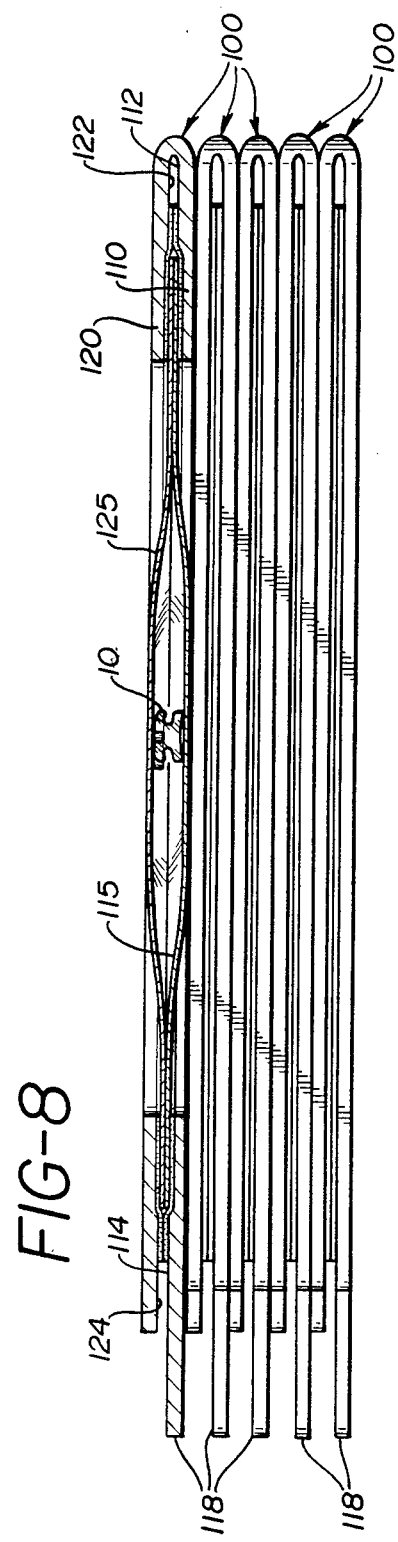
FIG. 8 is a side elevation view in cross section of a number of protective strips of the present invention placed one on top of the other.

As further seen in FIG. 7, the holders 100 of the invention are configured such that they can be stacked one on top of the other, akin to photographic slides. In other words, the frames 110, 120 of the holder 100 should be thicker than the dental brackets 10. When the holder 100 is folded, the plastic sealants 115, 125 are stretched across the frames 110, 120 and form a pouch holding the dental bracket 10. In this manner, it is the folded holder 100 onto which the other folded holders 100 are stacked. The dental bracket 10 is held in the pouch between the thickness of the folded frames 110, 120. The folded frames 110, 120 form a planar surface and are stacked on top of each other. In this manner, a number of dental brackets can be collected, and stacked, stored and transported together so that an entire set of dental brackets for the mouth is available at the same time to the user.

Figure 3:
FIG. 3 is a side view of a closed dental bracket of the present invention when emplaced on a retaining strip as in FIG. 1.
Figure 4:
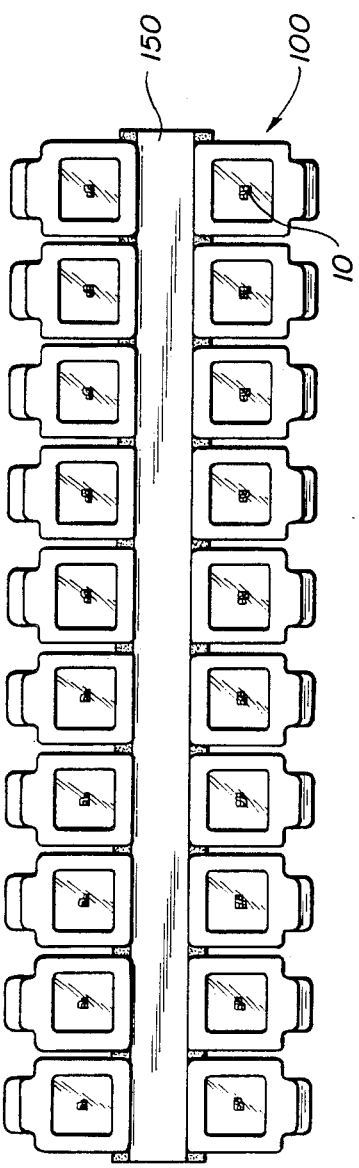
FIG. 4 is a top view of a plurality of dental brackets maintained on a adhesive strip in accordance with the principles of the present invention.

In addition, other aspects of the present invention allow all the dental brackets to be stored on a separate card. This is accomplished by the strip 150 as seen in FIGS. 1, 3 and 4. This strip 150 has a pair of elongated sides 155, 255, and on one face of the strip adhesive is placed. This adhesive surface of the strip 150 will adherently hold an entire oral set of dental brackets within the holders 100. Thus, an entire set can be placed on a card-shaped form, and again, the brackets will be easily manageable.

Figure 6:
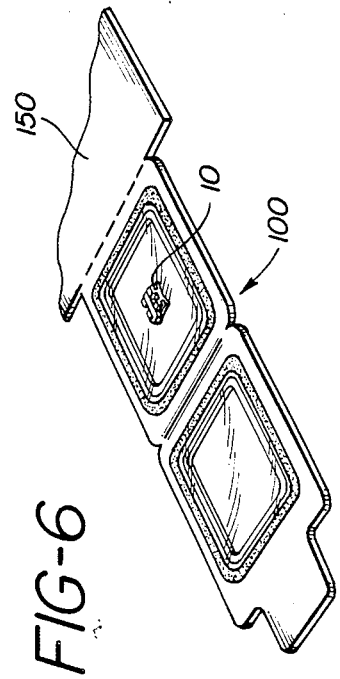
FIG. 6 is a perspective view of a second alternate preferred embodiment of the present invention on a retaining strip.
Figure 5:
FIG. 5 is a perspective view of an alternate preferred embodiment of the present invention when placed on an adhesive strip.

Of course, it will be realized that the strip need not be centrally located, but may also surround the holders as a large rectangular surface, or even hold only one set of holders 100, and be more elongated. As seen in FIG. 5, handles 118 can be attached to strip 150 and the frames 110 and 120 can open outwards so that the strip 150 prevents the handles from inadvertently opening during use. Of course, the strip 150 and frames 110, 120 can be formed of a single unitary piece of tear resistant cardboard, as seen in FIG. 6. Therefore, the dental brackets 100 can be placed within the folded frames 110, 120 all within the same card-shaped device.

Thus, while the present invention has been described in accordance with this specifically preferred embodiment, it is of course, understood that the invention is comprised of the presently appended claims and their equivalents.

What is claimed is:

1. A system for holding dental brackets comprising:
    an elongated strip having two sides and onto which are removably attached a plurality of tear-proof frames;
    each said tear-proof frame having an adhesive coated to one side, said frame symmetrically configured about a central line and wherein said frame is rectangular in shape and contains a pair of parallel first strips, each said first strip having a pair of parallel sides, each said first strip connected by a second pair of parallel strips, each said second strip having a pair of parallel sides;
    a puncture-proof, transparent sealant attached to said frame within the boundaries formed by said frame, into which said dental bracket is emplaced, such that when said frame is folded about said central line, said sealant forms a pouch surrounding said dental bracket and said symmetrical frame parts adhere to themselves, sealing said dental bracket within said pouch; and
    wherein the thickness of said folded frame is greater than said pouch with said dental bracket contained therein, such that said folded frame forms a pair of planar surfaces to enable stacking on said planar surfaces with said pouch holding said dental bracket between said planar surfaces.

2. The system of claim 1 wherein each said frame is a plastic coated cardboard.

3. The system of claim 1 wherein said each frame is square when folded.

4. The system of claim 1 wherein the sealant is plastic.

5. The holder of claim 4 wherein the sealant is polyvinyl.

6. A system for holding dental brackets comprising:
    a carrying strip having a pair of elongated parallel sides in proximity to each other, a plurality of tear-proof frames attached to one of said carrying strip sides, each said frame symmetrically configured about a central line;
    wherein each said frame is rectangular in shape and contains a pair of parallel first strips, each said first strip having a pair of parallel sides, each said first strip connected by a second shorter pair of parallel strips, each said shorter second strip having a pair of parallel sides;
    a puncture-proof, transparent sealant attached to said frame within the boundaries formed by each said frame, into which one of said dental brackets is emplaced, such that when said frame is folded about said central line, said sealant forms a pouch surrounding said dental bracket and said symmetrical frame parts adhere to themselves, sealing said dental bracket within said pouch; and
    wherein the thickness of said folded frame is greater than said pouch with said dental bracket contained therein, such that said folded frame forms a pair of planar surfaces to enable stacking on said planar surfaces with said pouch holding said dental bracket between said planar surfaces.

7. The system of claim 6 wherein said frames are removably attached to said rectangular strip by means of an adhesive.

8. The system of claim 7 wherein said plurality of tear-proof frames are attached to both of said parallel elongated strip sides.

* * * * *